(12) United States Patent
Chen

(10) Patent No.: US 10,098,777 B2
(45) Date of Patent: Oct. 16, 2018

(54) ANKLE STIRRUP

(71) Applicant: Tung-Cheng Chen, Taichung (TW)

(72) Inventor: Tung-Cheng Chen, Taichung (TW)

( * ) Notice: Subject to any disclaimer, the term of this patent is extended or adjusted under 35 U.S.C. 154(b) by 439 days.

(21) Appl. No.: 14/935,369

(22) Filed: Nov. 6, 2015

(65) Prior Publication Data

US 2017/0128250 A1    May 11, 2017

(51) Int. Cl.
    *A61F 5/01*    (2006.01)

(52) U.S. Cl.
    CPC .................. *A61F 5/0127* (2013.01)

(58) Field of Classification Search
    CPC ............................ A61F 5/0127; A61F 5/0111
    USPC .......................................................... 602/27
    See application file for complete search history.

(56) References Cited

U.S. PATENT DOCUMENTS

| 552,143 | A | * | 12/1895 | Rankin | ................. | A61F 5/0123 |
| | | | | | | 602/16 |
| 1,007,567 | A | * | 10/1911 | Holder | ................. | A61F 5/0123 |
| | | | | | | 602/16 |
| 4,776,326 | A | * | 10/1988 | Young | ................. | A61F 5/0102 |
| | | | | | | 602/16 |
| 5,865,778 | A | * | 2/1999 | Johnson | ................. | A43B 7/20 |
| | | | | | | 36/88 |
| 6,350,246 | B1 | * | 2/2002 | DeToro | ................. | A61F 5/0127 |
| | | | | | | 128/882 |
| 2010/0030123 | A1 | * | 2/2010 | DeToro | ................. | A61F 5/0127 |
| | | | | | | 602/28 |
| 2013/0296754 | A1 | * | 11/2013 | Campbell | ............. | A61F 5/0123 |
| | | | | | | 602/16 |

* cited by examiner

*Primary Examiner* — Tarla Patel
(74) *Attorney, Agent, or Firm* — Hershkovitz & Associates, PLLC; Abe Hershkovitz

(57) ABSTRACT

An ankle stirrup has a base, an ankle holder, a holder extender, and four combination structures. The ankle holder is pivotally combined with the base. The holder extender is pivotally combined with the ankle holder and located over the ankle holder. The four combination structures are disposed on the base, the ankle holder, and the holder extender to combine with the base, the ankle holder, and the holder extender. The ankle stirrup can achieve a fixing effect for an ankle of a user.

2 Claims, 6 Drawing Sheets

ANKLE STIRRUP

BACKGROUND OF THE INVENTION

1. Field of the Invention

The present invention relates to a stirrup, and more particularly to an ankle stirrup.

2. Description of Related Art

A conventional ankle stirrup comprises a base and an ankle holder. The ankle holder is pivotally combined with the base. In use, the ankle holder is mounted around a leg of a user, such that the ankle stirrup can fix an angle of an ankle of the user.

The ankle holder is integrally formed as an upright holder, such that the ankle holder can be mounted around the whole leg to achieve a fixing effect for the ankle of the user. However, leg sizes and lengths of different users differ from each other, such that the integrally formed ankle holder cannot be suitable for legs of different users. When the user wears the ankle stirrup, a size of the ankle holder cannot match the size of the leg of the user, such that the fixing effect for the leg of the user will be decreased.

SUMMARY OF THE INVENTION

The main objective of the present invention is to provide an improved ankle stirrup to resolve the afore-mentioned problems.

The ankle stirrup comprises a base, an ankle holder, a holder extender, and four combination structures.

The ankle holder is pivotally combined with the base.

The holder extender is pivotally combined with the ankle holder and is located over the ankle holder.

The four combination structures are disposed on the base, the ankle holder, and the holder extender to combine with the base, the ankle holder, and the holder extender. Two of the combination structures are disposed on the base and the ankle holder, such that the ankle holder is pivotally combined with the base. The other two combination structures are disposed on the ankle holder and the holder extender, such that the holder extender is pivotally combined with the ankle holder. Each combination structure comprises a hook portion and two fixing grooves functionally disposed on the base, the ankle holder, and the holder extender, such that the hook portion is selectively combined with one of the fixing grooves.

Other objectives, advantages and novel features of the present invention will become more apparent from the following detailed description when taken in conjunction with the accompanying drawings.

BRIEF DESCRIPTION OF THE DRAWINGS

FIG. 2A is an enlarged perspective view of the ankle stirrup in FIG. 2;

DETAILED DESCRIPTION OF PREFERRED EMBODIMENT

Figure 1:
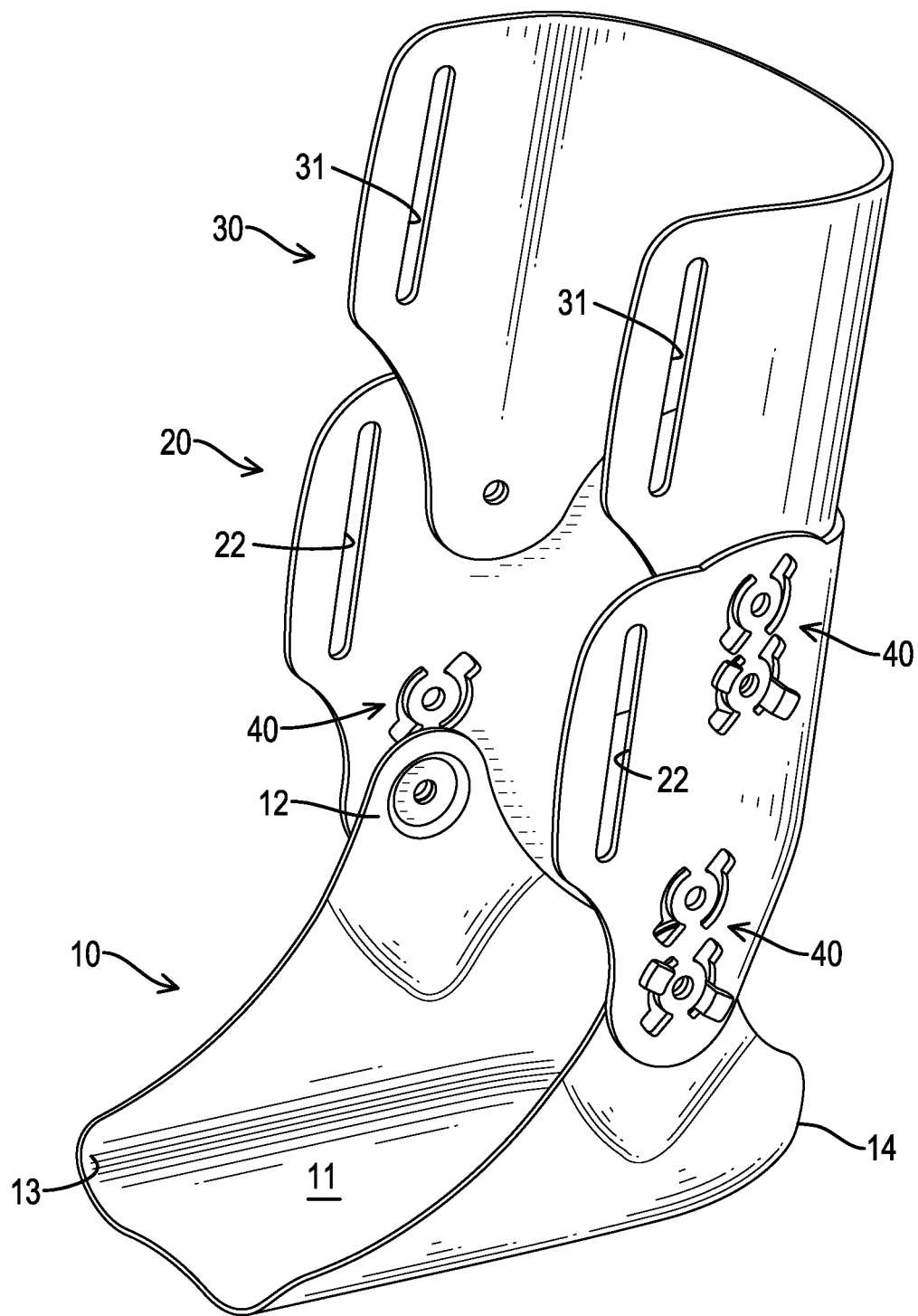
FIG. 1 is a perspective view of a preferred embodiment of an ankle stirrup in accordance with the present invention.
Figure 2:
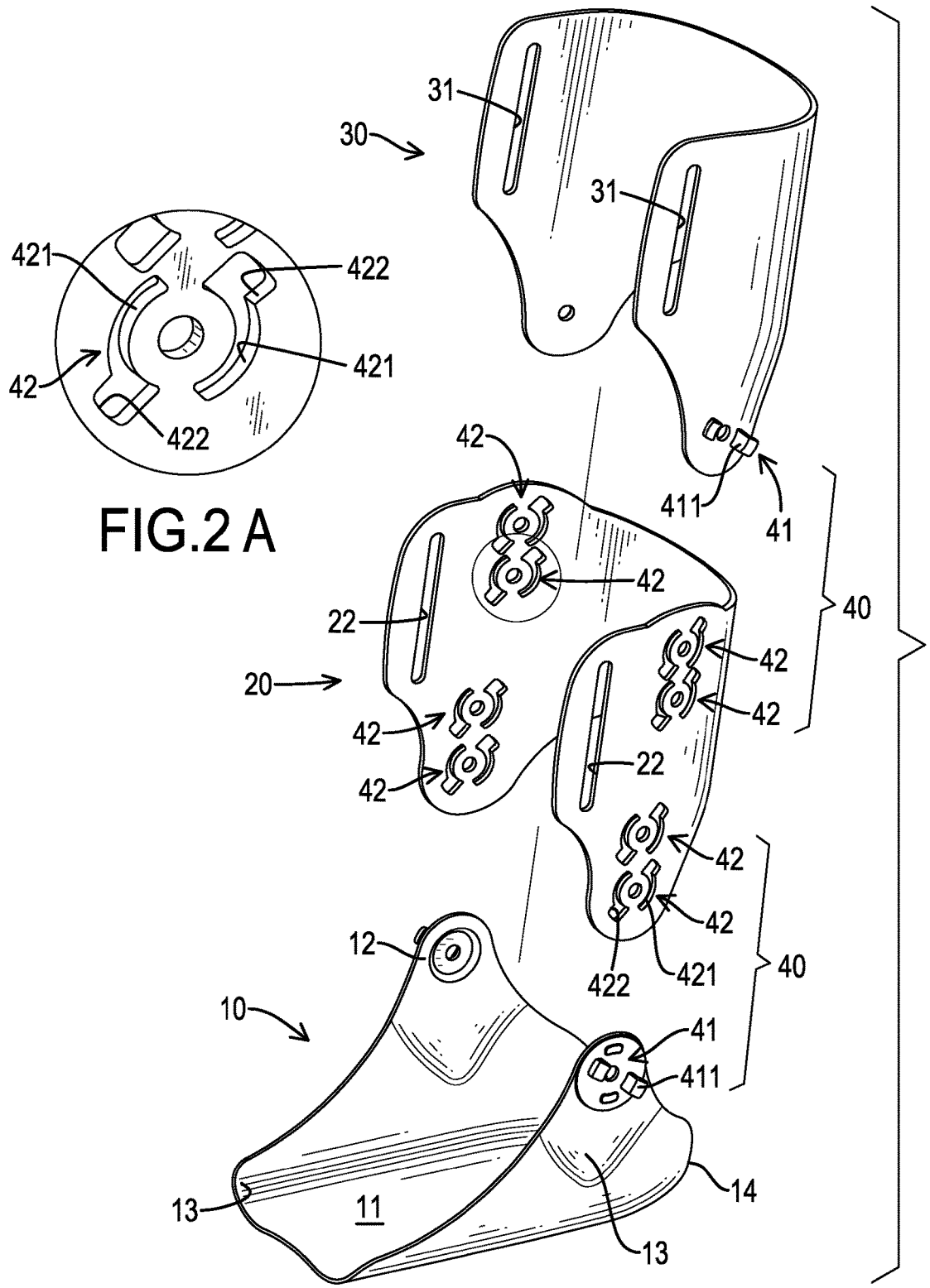
FIG. 2 is an exploded perspective view of the ankle stirrup in FIG. 1.
Figure 3:
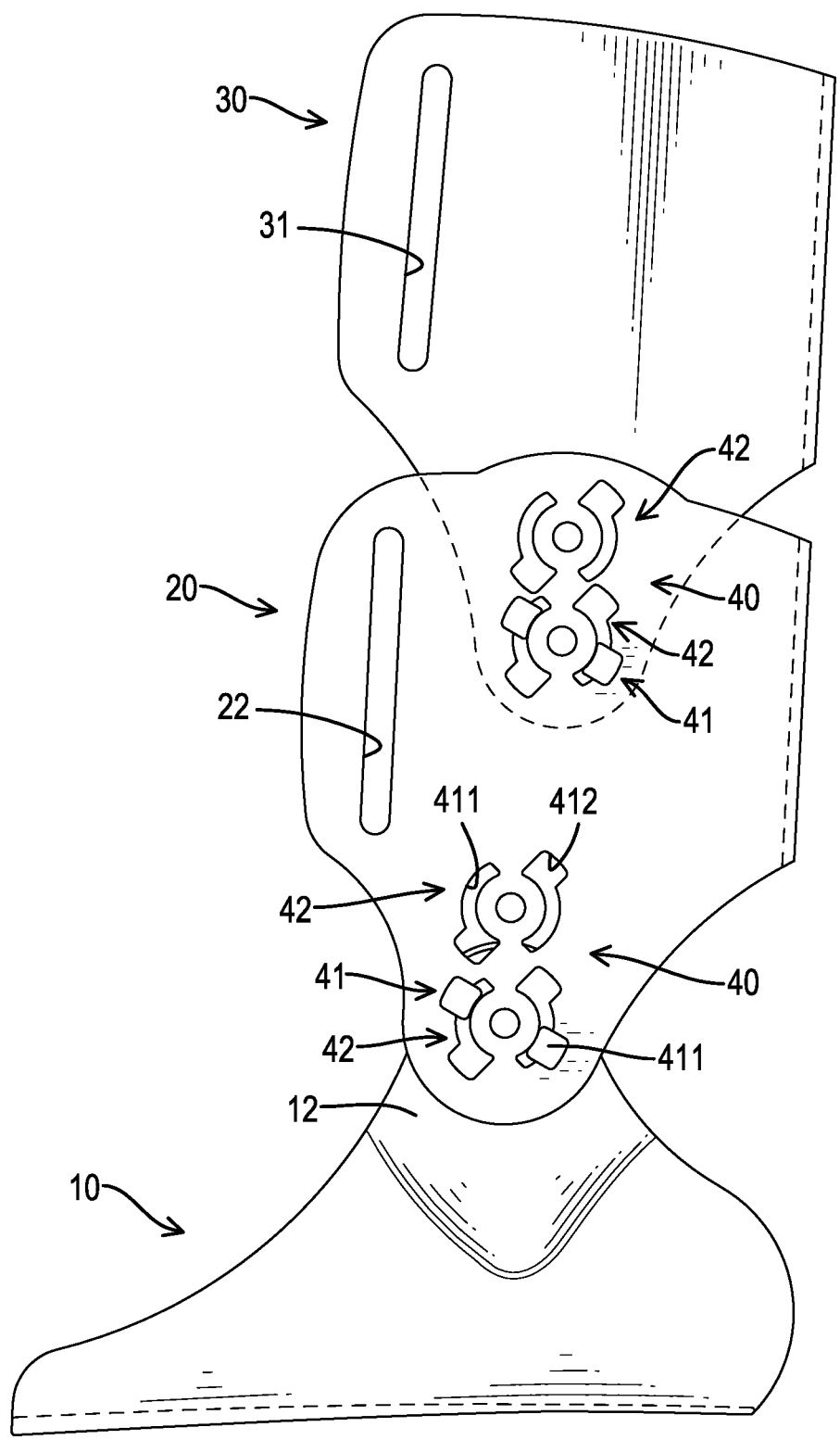
FIG. 3 is a side view of the ankle stirrup in FIG. 1.

With reference to FIGS. 1 to 3, a preferred embodiment of an ankle stirrup in accordance with the present invention comprises a base 10, an ankle holder 20, a holder extender 30, and four combination structures 40.

The base 10 comprises a foot space 11 and two combination plates 12. The foot space 11 is surrounded by the base 10, such that the base 10 is formed in a U shape. The foot space 11 comprises a front opening 13 and a rear opening 14. The front opening 13 is formed in a front of the base 10, and the rear opening 14 is formed in a rear of the base 10. In use, a foot of a user is inserted into the foot space 11, a heel of the user is located at the rear opening 14, and toes of the user are located at the front opening 13. The combination plates 12 are formed on a top of the base 10, and are respectively located at a right side and a left side of the foot space 11.

Further with reference to FIGS. 2 and 2A, the ankle holder 20 is pivotally combined with the combination plates 12 of the base 10, and comprises two belt slits 22. The ankle holder 20 is formed in a U shape, and comprises a rear side, a right side, and a left side. In use, the ankle holder 20 is mounted around a leg of the user, and the rear side of the ankle holder 20 corresponds in position to a rear side of the leg, and the right side and the left side of the ankle holder 20 respectively correspond in position to a right side and a left side of the leg. The belt slits 22 are respectively formed through the right side and the left side of the ankle holder 20.

The holder extender 30 is pivotally combined with the ankle holder 20, is located over the ankle holder 20, is formed in a U shape, and comprises a rear side, a right side, a left side, and two belt slits 31. The rear side, the right side, and the left side of the holder extender 30 correspond in position to the rear side, the right side, and the left side of the ankle holder 20 respectively. The belt slits 31 are respectively formed through the right side and the left side of the holder extender 30.

The combination structures 40 are disposed on the base 10, the ankle holder 20, and the holder extender 30 to combine the base 10, the ankle holder 20, and the holder extender 30 with each other. Two of the combination structures 40 are disposed on the two combination plates 12 and a lower half of the ankle holder 20 to combine the base 10 with the ankle holder 20. The other two combination structures 40 are disposed on the ankle holder 20 and the holder extender 30 to combine the ankle holder 20 with the holder extender 30. Each combination structure 40 comprises a hook portion 41 and two fixing grooves 42 functionally disposed on the base 10, the ankle holder 20, and the holder extender 30. Positions of the hook portion 41 and the fixing groove 42 are not limited in the referenced application. Preferably, the hook portions 41 are disposed on the base 10 and the holder extender 30, and the fixing grooves 42 are disposed on the ankle holder 30. Each one of the hook portions 41 is combined with a corresponding fixing groove 42.

The following descriptions use one of the combination structures 40 to explain the combination between the base 10 and the ankle holder 20, or between the ankle holder 20 and the extender holder 30. The two fixing grooves 42 of one of the combination structures 40 are respectively disposed at an upper position and a lower position. Each fixing groove 42 comprises two fixing paths 421 and two insertion entries 422. The fixing paths 421 are disposed at two opposite positions along a circumferential direction, and the insertion entries 422 respectively communicate with the fixing paths 421, and are also disposed at two opposite positions along the same circumferential direction. The hook portion 41 comprises two hooks 411 disposed at two opposite positions along another circumferential direction. The hook portion 41 is selectively combined with one of the fixing grooves 42, wherein the hooks 411 of the hook portion 41 are respectively combined with the fixing paths 421 of the corresponding fixing groove 42.

In assembling, the ankle holder 20 is pivotally combined with the base 10. The hooks 411 disposed on the base 10 are respectively inserted into the corresponding insertion entries 422 disposed on the ankle holder 20, and then the ankle holder 20 is pivoted relative to the base 10, such that the hooks 411 can be inserted into the corresponding fixing paths 421. The holder extender 30 is pivotally combined with the ankle holder 20. The hooks 411 disposed on the holder extender 30 are respectively inserted into the corresponding insertion entries 422 disposed on the ankle holder 20, and then the holder extender 30 can be pivoted relative to the ankle holder 20.

Figure 4:
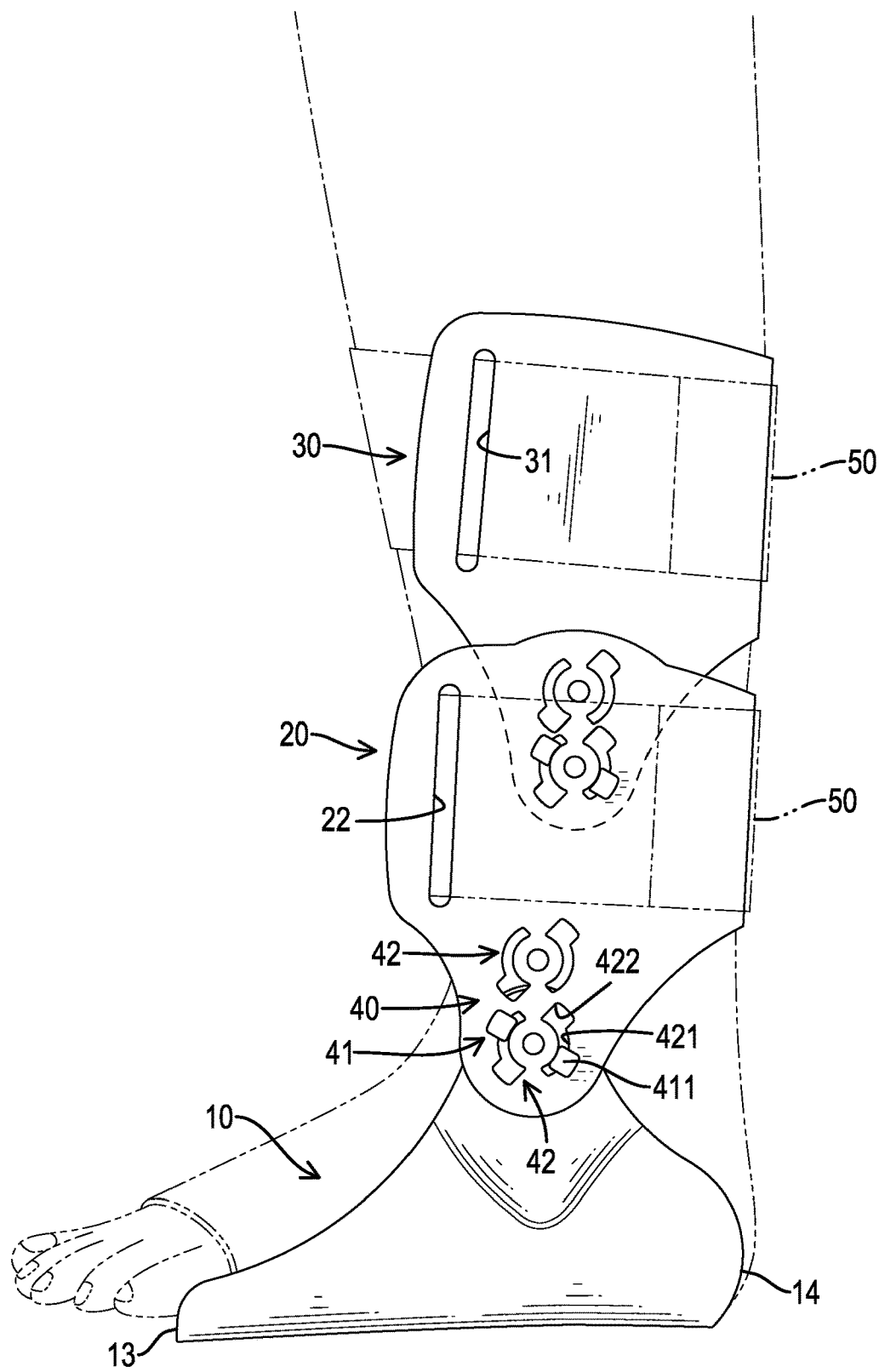
FIGS. 4 to 6 are different operational side views of the ankle stirrup in FIG. 1.

In use, with reference to FIG. 4, a foot and a leg of a user are inserted into the ankle stirrup. Two belts 50 are respectively inserted into the belt slits 22 and the belt slits 31 to fix the ankle holder 20 and the holder extender 30 around the leg of the user. The ankle holder 20 is mounted around the leg of the user. A mounting angle of the ankle holder 20 relative to the base 10 can be adjusted to be suitable for the ankle and the leg of the user. A mounting angle of the holder extender 30 relative to the ankle holder 20 can be adjusted to be suitable for the leg of the user. After the wearing process of the ankle stirrup is finished, the mounting angles of the ankle holder 20 and the holder extender 30 are fixed to protect the ankle of the user.

Figure 5:
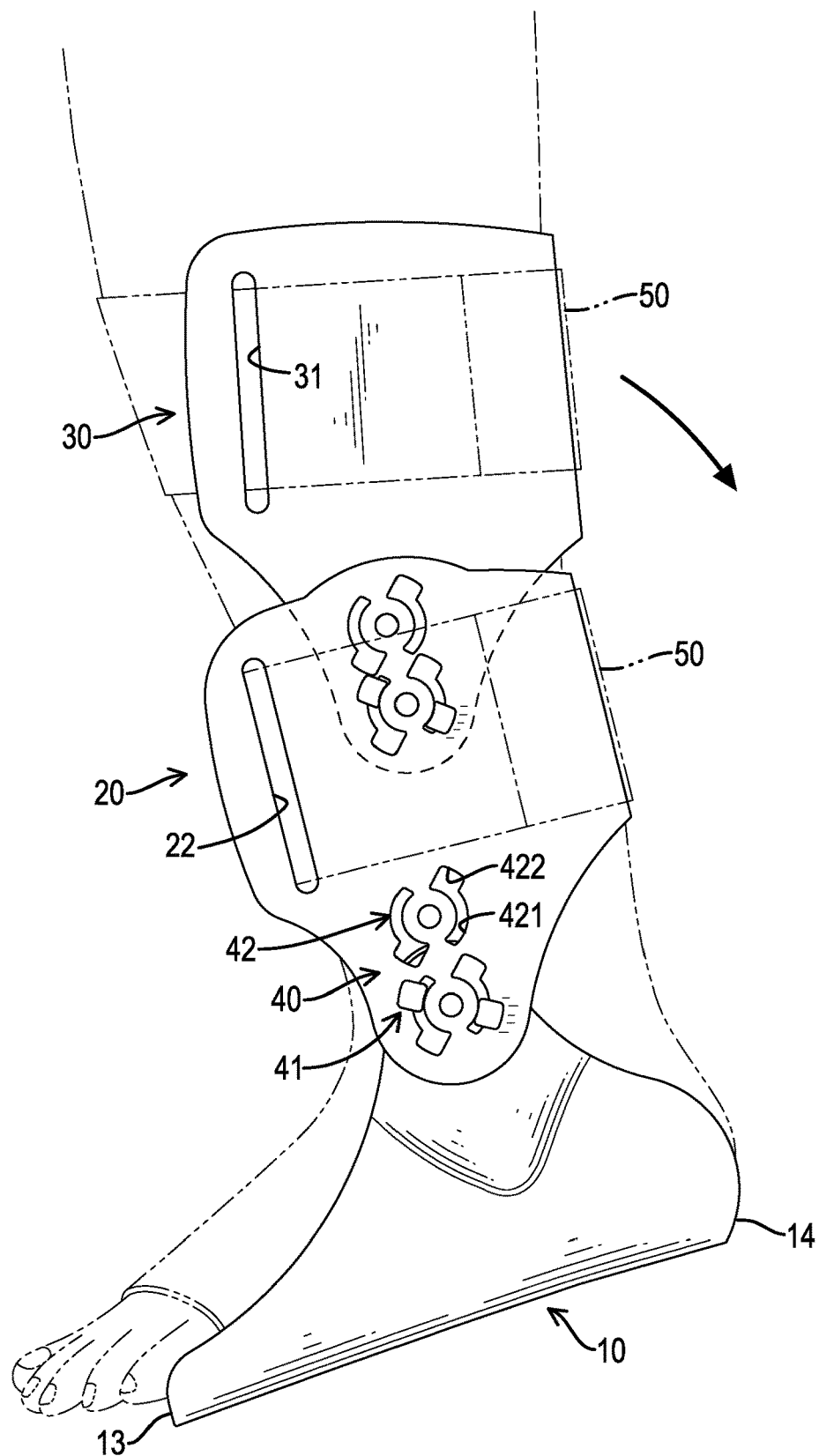

With reference to FIG. 5, before the wearing process of the ankle stirrup is finished, the mounting angle of the holder extender 30 relative to the ankle holder 20 can be adjusted to be suitable for a leg of another user. When the mounting angle of the holder extender 30 relative to the ankle holder 20 is adjusted, the hooks 411 disposed on the holder extender 30 are moved along the corresponding fixing paths 421 to fix the mounting angle of the holder extender 30.

Figure 6:
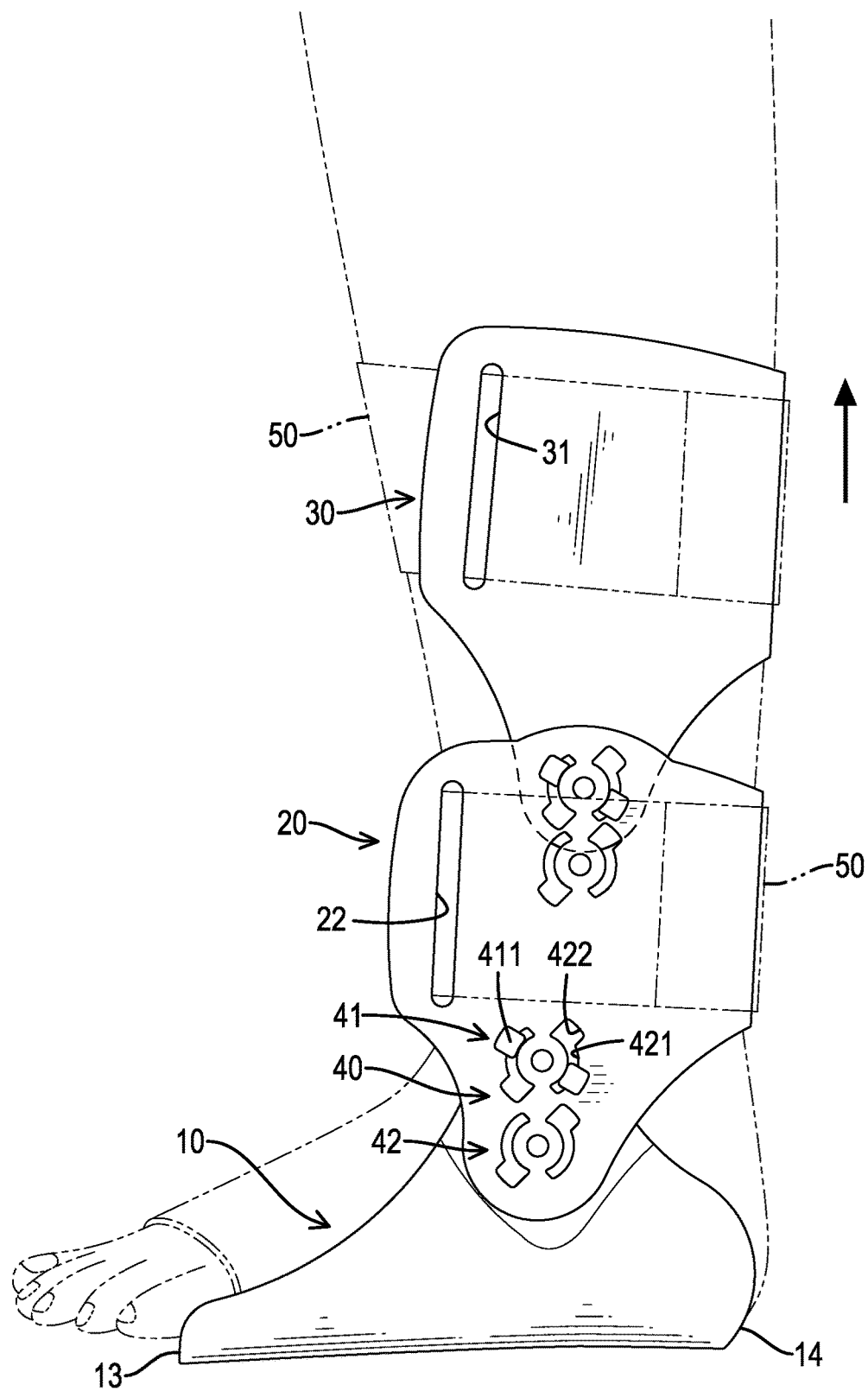

With reference to FIG. 6, the hooks 411 disposed on the holder extender 30 are combined with the fixing paths 421 of the fixing groove 42 disposed at the upper position on the ankle holder 20 to adjust a height of the ankle stirrup to be suitable for a leg of another user.

From the over description, it is noted that the present invention has the following advantages: before the wearing process of the ankle stirrup is finished, the ankle holder 20 can be pivoted relative to the base 10, and the holder extender 30 also can be pivoted, such that the mounting angles of the ankle holder 20 and the holder extender 30 can be adjusted for the leg sizes of different users. The ankle holder 20 can be combined with the base 10 on an upper position or on a lower position, and the holder extender 30 also can be combined with the ankle holder 20 on an upper position or on a lower position by the combination structures 40. When the hooks 411 are combined with the fixing grooves 42 that are disposed on the lower positions, the height of the ankle stirrup is decreased. Alternatively, when the hooks 411 are combined with the fixing grooves 42 that are disposed on the upper positions, the height of the ankle stirrup is increased. Therefore, the height of the ankle stirrup can be suitable for the leg lengths of different users. As a result, the ankle stirrup of the present invention indeed can achieve an improved fixing effect for the ankle of the user.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An ankle stirrup comprising:
   a base;
   an ankle holder pivotally combined with the base;
   a holder extender pivotally combined with the ankle holder and located over the ankle holder; and
   four combination structures disposed on the base, the ankle holder, and the holder extender to combine the base, the ankle holder, and the holder extender with each other, wherein
      two of the combination structures are disposed on the base and the ankle holder, such that the ankle holder is pivotally combined with the base;
      the other two combination structures are disposed on the ankle holder and the holder extender, such that the holder extender is pivotally combined with the ankle holder;
      each one of the combination structures comprises a hook portion and two fixing grooves functionally disposed on the base, the ankle holder, and the holder extender, such that the hook portion is selectively combined with one of the fixing grooves:
   the hook portion of each combination structure comprises two hooks disposed at two opposite positions along a first circumferential direction;
   each fixing groove comprises
      two fixing paths disposed at two opposite positions along a second circumferential direction; and
      two insertion entries respectively communicating with the fixing paths, and also disposed at two opposite positions along the second circumferential direction; and
   each hook portion is selectively combined with a corresponding one of the fixing grooves, wherein the hooks of the hook portion are respectively combined with the fixing paths of the corresponding fixing groove.

2. The ankle stirrup as claimed in claim 1, wherein the fixing grooves of the combination structures are disposed on the ankle holder, and the hook portions of the combination structures are disposed on the base and the holder extender.

* * * * *